United States Patent [19]

Schwartz

[11] Patent Number: 5,513,652
[45] Date of Patent: May 7, 1996

[54] MALE ERECTION FACILITATION SHEATHS AND METHODS OF USING SAME

[76] Inventor: Alan N. Schwartz, 19211-93rd Pl. W., Edmonds, Wash. 98020

[21] Appl. No.: 912,683
[22] Filed: Jul. 13, 1992
[51] Int. Cl.⁶ .................................. A61F 6/02; A61F 6/04
[52] U.S. Cl. ........................... 128/842; 128/844; 128/918
[58] Field of Search .................................. 128/842, 844, 128/918; 604/330, 347–353

[56] References Cited

U.S. PATENT DOCUMENTS

| | | | |
|---|---|---|---|
| 2,586,674 | 2/1952 | Lönne | 128/844 |
| 4,798,600 | 1/1989 | Meadows | 128/844 |
| 4,881,553 | 11/1989 | Grossman | 128/844 |
| 4,919,149 | 4/1990 | Stang | 128/844 |
| 4,987,905 | 1/1991 | Broad | 128/844 |
| 5,027,802 | 7/1991 | Donohue | 602/22 |
| 5,109,871 | 5/1992 | Thornton | 128/844 |
| 5,121,755 | 6/1992 | Hegedusch | 128/844 |
| 5,137,032 | 8/1992 | Harmon | 128/844 |

Primary Examiner—Michael A. Brown
Attorney, Agent, or Firm—Graybeal Jackson Haley & Johnson

[57] ABSTRACT

Prophylactic devices, including devices for assisting and establishing and maintaining male erectile function, are disclosed. Devices and methods for facilitating male erectile function include open ended elastic sheaths having a plurality of woven strands in open weave configuration wherein the strands are movable longitudinally and individually of one another, with the sheath causing selective constriction around and/or along selected portions of the penis by differential external pressures applied to said selected portions so as to not impede arterial blood flow to the penis but impede venous blood flow from the penis and thereby establish and maintain the penis in an erectile position. Forms are also disclosed wherein venous blood flow is selectively impeded by the device having circumferentially disposed tapered portions or by having less elasticity or thickened chambers in some portions. Other devices are also disclosed including condoms with liquid retaining chambers for dispensing medication or the like.

11 Claims, 4 Drawing Sheets

MALE ERECTION FACILITATION SHEATHS AND METHODS OF USING SAME

BACKGROUND OF THE INVENTION

The invention pertains to devices for assisting erectile function, for prosthetic use, for a dispensing of medicine or the like, and for partitioning of bodily fluids during intercourse. More specifically, the present invention pertains to devices of the above type which are condoms.

Normal erectile function requires numerous physiologic events to occur in concert. First, adequate neuro-psychogenic, chemical or electrical stimulus must be present. Second, there must be adequate arterial inflow into the penis. Third, the corporal, smooth muscles must relax and corporal epithelial tissue must respond to the erectile stimulus, thus allowing the corporal sinusoids to expand and fill with blood. Finally, the venous closure mechanism must be initiated to prevent outflow of blood, thus resulting in storage of blood within the corpora cavernosum.

The penis is divided into four hydraulic chambers. Two corpora cavernosa straddles the corpus spongiosum. These chambers are crowned by the glans penis. The two corpora cavernosa are responsible for erections. Each corpora cavernosa is supplied by a cavernosal artery. The cavernosal artery flow and pressure determine the arterial competence of the erectile process. As the blood fills and expands these hydraulic chambers, the corporal venules and penile veins are compressed. This compression increases outflow resistance, permitting blood to flow into but not out of the corpora cavernosa. Intracorporal resistance is usually between about 5 to 10 mmHg×min/ml. Tumescence and rigidity results as blood is increasingly stored within the corpora cavernosa. Early in tumescence, intracorporal pressure is about 10 mmHg. During full tumescence, intracorporal pressure is between about 90 and 150 mmHg. Borderline erectile function is available at about 50 mmHg. Detumescence occurs when arterial inflow decreases, or corporal outflow increases, resulting in a net loss of blood from the penis. Some males are unable to obtain or sustain an adequate erection because sufficient intracorporal pressure cannot be achieved or maintained.

A need thus exists for a facilitator which is able to assist borderline erectile function of about 50 mmHg intracorporal pressure by providing external pressure onto the penis to produce a transmitted internal pressure change sufficient to increase intracorporal pressure in the penis such that normal erectile function can be achieved or maintained.

A need exists for the above type of facilitator for assisting erectile function in which weaves, tapered portions, portions of lesser elasticity, thickened portions, and chambers retaining solids or liquids are employed.

A need also exists for the above type of facilitator in which a liquid retaining chamber for dispensing medication or the like is included.

A need also exists for the above type of facilitator in which bodily fluids are partitioned during intercourse by means of a plurality of circumferentially disposed annular ribs on the interior of the facilitator.

SUMMARY OF THE INVENTION

In a first embodiment of a facilitator for assisting erectile function, a plurality of woven strands maintain elongation or expansion of an erect penis by constricting around or along the penis to impede venous blood flow from the penis. Preferably, the strands are interwoven both longitudinally on, and axially around, the facilitator. However, the strands may be interwoven only longitudinally on, or axially around, the facilitator.

In a second embodiment of a facilitator for assisting erectile function, a tapered portion having a diameter less than an erect penis maintains erection of the penis by imparting an external pressure onto the penis to impede venous blood flow therethrough. Preferably, the tapered portion is located at the base portion of the facilitator; however, this tapered facilitator may also be located at the central or distal portions of the facilitator.

In a third embodiment of a facilitator for assisting erectile function, a circumferentially disposed portion with a degree of elasticity less than the degree of elasticity of the rest of the condom maintains an erection by imparting an external pressure onto the penis to impede venous blood flow therefrom. Preferably, the circumferentially disposed portion is located at the base of the facilitator.

In a fourth embodiment of a facilitator which functions as a prosthesis and assists erectile function, a portion of the facilitator has a thickness greater than the remainder of the facilitator such that the thickened portion has a lesser degree of elasticity. In this manner, the facilitator functions as a penile prosthesis and maintains erection by imparting an external pressure onto the penis to impede venous blood flow therefrom. This thickened portion is preferably circumferentially disposed on the condom and contains either a fluid or a solid. In this embodiment of a facilitator which assists erectile function, an internal chamber in the thickened portion may be adapted to be filled with a fluid by the user such that an external pressure is imparted onto the penis to impede venous blood flow therefrom. The internal chamber is preferably circumferentially disposed around the facilitator.

In a fifth embodiment in the form of a condom, medication or the like is dispensed onto the penis from a liquid retaining chamber. Means for initially partitioning and for subsequently providing communication between the liquid retaining chamber and the condom allows dispensing of the medication or the like. Preferably, a plurality of channels connect the condom and the liquid retaining chamber. Preferably, the liquid retaining chamber is located at the tip of the condom; however, it may also be located at the base thereof, or in channels thereon. Preferably, the means for initially partitioning and for subsequently providing communication between the condom and the liquid retaining chamber is a one-way valve comprised of an area of elastomeric material having an orifice in the center thereof.

In the sixth embodiment in the form of a condom, bodily fluids are partitioned during intercourse by a plurality of annular ribs circumferentially disposed on the interior side of the condom, preferably, the annular ribs are located at either or both of the base portion and the central portion of the condom. Most preferably, the ribs located adjacent the base are angled toward the base, and the ribs located adjacent the central portion are angled toward the tip. In this manner, semen is retained in the condom and vaginal fluids are excluded therefrom.

In a seventh embodiment in the form of a condom, the condom is sheathed with a layer of hydrophobic or hydrophilic material to decrease the frictional coefficient during intercourse.

BRIEF DESCRIPTION OF THE DRAWINGS

The foregoing objects and the attendant advantages of this invention will become more readily appreciated as the same becomes better understood by reference to the following detailed description when taken in conjunction with the accompanying drawings wherein.

DETAILED DESCRIPTION OF THE PREFERRED EMBODIMENTS

Figure 1:
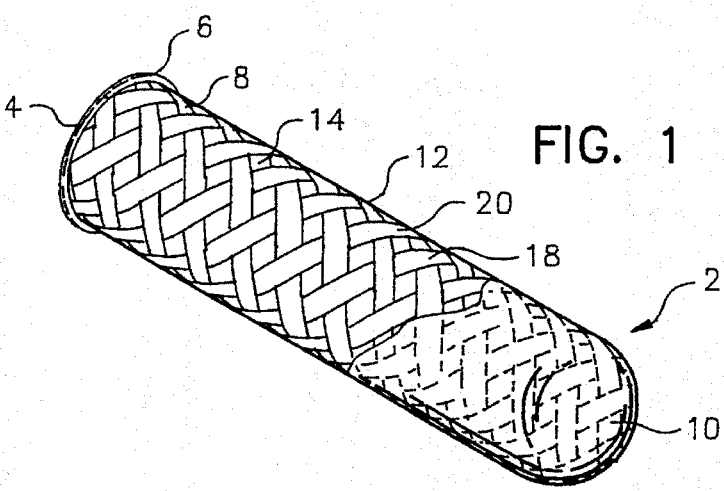
FIG. 1 is a perspective view of a first embodiment of the present invention showing a first weave pattern.

Referring to FIGS. 1–22, the device for assisting erectile function is preferably a facilitator 2 having an open end 4 with a rim 6 circumferentially disposed therearound on base 8. Facilitator 2 also has a closed tip 10 and a central portion 12, as well as external surface 14 and internal surface 16. While the device for assisting erectile function of the present invention is preferably condom 2, where birth control and prevention of sexually transmitted disease are not factors, closed tip 10 can be absent such that the device of the present invention is an open-ended sleeve (not shown). Facilitator 2 is preferably formed of latex, any other synthetic polymer or any other material employed in prophylactics.

While all of the below embodiments of the present invention are described individually, it is to be understood that one or more of said embodiments can be combined to optimize the assistance of erectile function; the dispensing of medicine, spermicide, or bactericide; and the partitioning of bodily fluids during intercourse.

Figure 2:
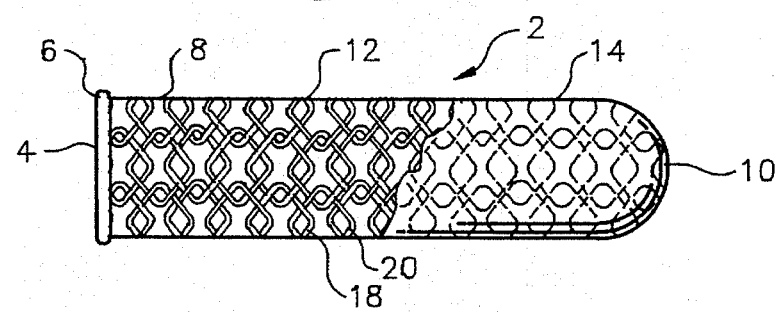
FIG. 2 is a plan view of the first embodiment of the present invention showing a second weave pattern.
Figure 3:
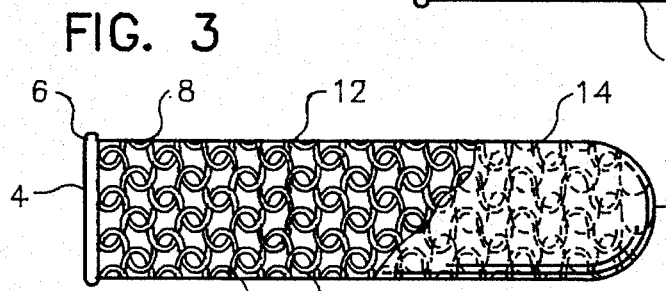
FIG. 3 is a plan view of the first embodiment of the present invention showing a third weave pattern.

Referring now to FIGS. 1–3, the first embodiment of the present invention for assisting erectile function is disclosed in which weave 18 is oriented over facilitator 2. Weave 18 may either be integral with, or bonded to, the latex of facilitator 2. Weave 18 is comprised of a plurality of fibers 20 formed of latex or other fibrous synthetic or natural material. In FIG. 1, fibers 20 comprising weave 18 are interwoven both longitudinally on, and axially around, facilitator 2. Thus, weave 18 maintains both elongation and expansion of an erect penis by constricting around and along the penis to impede venous blood flow therefrom.

Now referring to FIG. 2, weave 18 is comprised of fibers 20 which are interwoven only longitudinally on facilitator 2 such that weave 18 maintains elongation of an erect penis by constricting along the penis to impede venous blood flow therefrom.

In FIG. 3, weave 18 has fibers 20 which are interwoven only axially around facilitator 2. Thus, weave 18 maintains expansion of erect penis by constricting around the penis to impede venous blood flow therefrom.

As shown in FIGS. 1–3, numerous different types of weave 18 may be employed to maintain elongation and/or expansion of an erect penis. Specifically, weave 18 may be comprised of fibers 20 which are linear, sinusoidal, interlocking squares, interlocking circles, as well as numerous other configurations so long as the fibers are interwoven longitudinally and/or axially around facilitator 2. The length of fibers 20 on condom 2 are based upon the diameter of the flaccid penis such that the desired amount of constriction (external pressure) around or along the penis is imparted upon erection to impede venous blood flow. Weave 18 can cover either part or all of facilitator 2, depending on the amount of constriction (external pressure) desired, and the specific location of external pressure. The specific location of external pressure may be dependent upon the location of penile vascular dysfunction.

Figure 4:
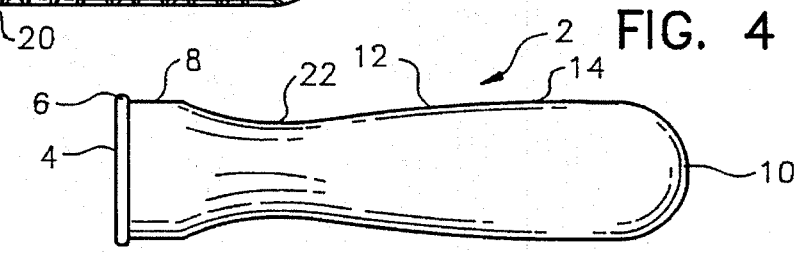
FIG. 4 is a plan view of a second embodiment of the present invention showing tapering at the central portion of the facilitator.
Figure 5:
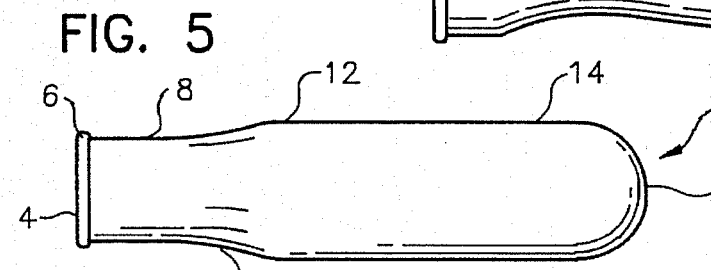
FIG. 5 is a plan view of the second embodiment of the present invention showing tapering at the base portion of the facilitator.

FIGS. 4 and 5 disclose a second embodiment of the present invention in which erectile function is assisted by tapered portion 22 on facilitator 2. Tapered portion 22 can be located at either central portion 12 or base portion 8 of facilitator 2, as shown in FIGS. 4 and 5, respectively. Tapered portion 22 can also be located at the distal portion of facilitator 2. Tapered portion 22 has a diameter less than that of the remainder of condom 2, and less than the diameter of the erect penis to maintain erection by imparting an external pressure onto the penis to impede venous blood flow therefrom. Tapered portion 22 is formed upon manufacture of the facilitator in a manner known in the art, and the diameter thereof is dictated by the relative size of the wearer's penis and the amount of external pressure desired.

Figure 6:
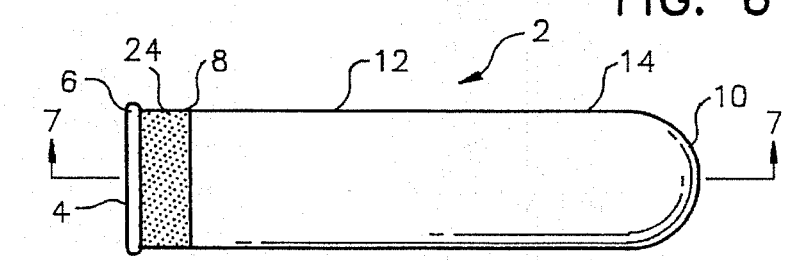
FIG. 6 is a plan view of a third embodiment of the present invention showing a band having a lesser degree of elasticity.

Referring now to FIG. 6, a third embodiment of the invention for assisting erectile function is shown in which facilitator 2 has, circumferentially disposed around base 8, a band 24 which is comprised of a material, such as a synthetic polymer, that has a degree of elasticity relatively less than the degree of elasticity over the remainder of facilitator 2. In this manner, an erection is maintained by imparting an external pressure onto the penis to impede venous blood flow therefrom. Thus, as the penis becomes erect, facilitator 2 expands therewith, while band 24 expands to a lesser degree, or not at all, such that external pressure is induced. Band 24 may be integral with, or bonded to, condom 2. The length and relative degree of elasticity of band 24 is determined by the relative diameter of the user's penis and the degree of external pressure desired to be imparted. While band 24 is shown around base 8, band 24 can be located anywhere on facilitator 2, and band 8 can cover any desired length of condom 2. Additionally, more than one band 8, spaced by predetermined distances, can be present.

Figure 7:
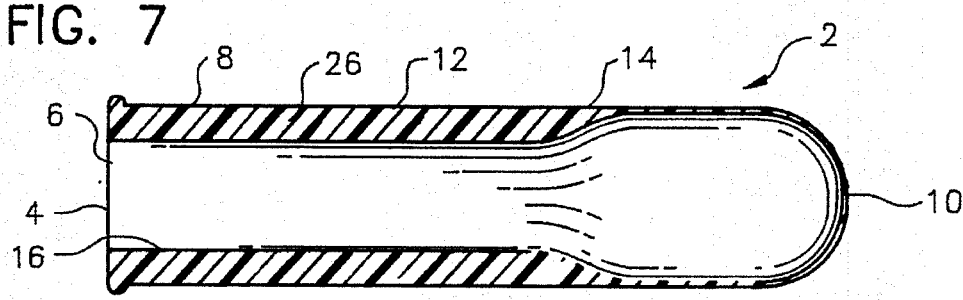
FIG. 7 is a cross-sectional view of a fourth embodiment of the present invention taken along lines 7—7 of FIG. 6 showing solid-filled chambers.
Figure 8:
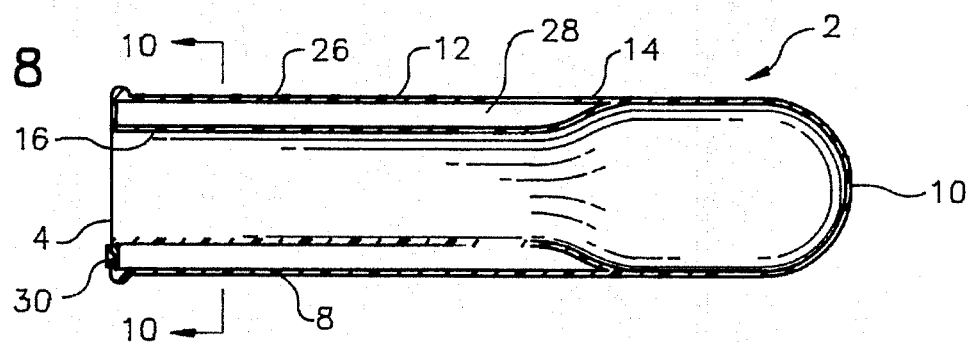
FIG. 8 is a cross-sectional view of the fourth embodiment of the present invention taken at the same location on FIG. 6 as FIG. 7 showing fluid-filled chambers.
Figure 9:
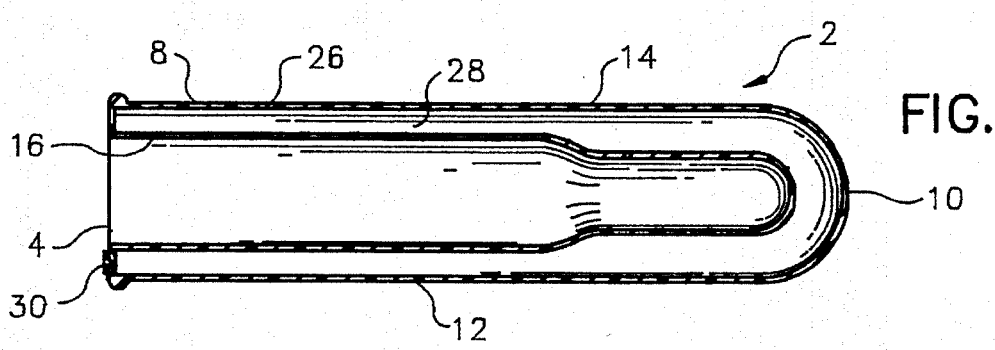
FIG. 9 is a cross-sectional view of the fourth embodiment of the present invention taken at the same location on FIG. 6 as FIG. 7 showing a chamber encompassing the entire length of the facilitator.

Referring now to FIGS. 7-13, a fourth embodiment of the invention for assisting erectile function is shown in which facilitator 2 also preferably functions as a prosthetic device for individuals who can only maintain a partial erection. Referring specifically to FIG. 7, condom 2 includes a thickened portion 26 having a depth greater than that of the remainder of facilitator 2, preferably between about 2 and 15 mm. In FIG. 7, thickened portion 26 is solid and is preferably comprised of a synthetic polymer such as latex or silicone. The relatively greater depth of thickened portion 26 results in a degree of elasticity less than that of the remainder of facilitator 2 such that an erection is maintained by imparting an external pressure onto the penis to impede venous blood flow therefrom. Additionally, the greater depth of thickened portion 26 provides structural support for the penis of individuals who can only obtain partial erections. Thus, facilitator 2 also functions as a prosthesis. The relative depth of thickened portion 26, as well as the relative elasticity of thickened portion 26 is determined by the relative diameter of the user's penis, the degree of external pressure desired to be imparted, as well as the amount of structural support desired. Referring now to FIGS. 8 and 9, the fourth embodiment of the invention for assisting erectile function which also operates as a prosthetic device can, in the alternative, have thickened portion 26 with internal chamber 28 therein. As opposed to the above described embodiment of FIG. 7 in which thickened portion 26 was solid, FIGS. 8 and 9 show thickened portion 26 which is filled with a gas or liquid in internal chamber 28 in order to provide external pressure and penile support. However, it is to be understood that a part of thickened portion 26 can be solid and a part can have a gas or liquid filled internal chamber 28 as well. Gas or liquid is admitted into internal chamber 28 via one-way valve 30 by means of a gas or liquid source known in the art. An example of a gas which can fill internal chamber 28 is air, while water, for example, is a liquid that can be used to fill internal chamber 28. The amount of gas or liquid employed to fill internal chamber 28 is determined by the relative diameter of the user's penis, the degree of external pressure desired to be imparted, and the amount of structural support needed.

Figure 10:
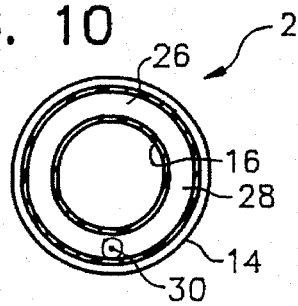
FIG. 10 is a cross-sectional view of the fourth embodiment of the present invention taken along lines 10—10 of FIG. 8 showing a first circumferential orientation of the chamber.
Figure 11:
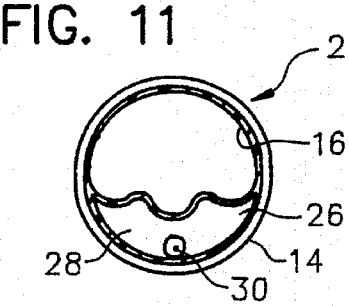
FIG. 11 is a cross-sectional view of the fourth embodiment of the present invention taken at the same location on FIG. 8 as FIG. 10 showing a second circumferential orientation of the chamber.
Figure 12:
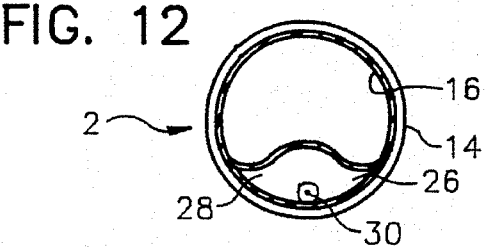
FIG. 12 is a cross-sectional view of the fourth embodiment of the present invention taken at the same location on FIG. 8 as FIG. 10 showing a third circumferential orientation of the chamber.
Figure 13:
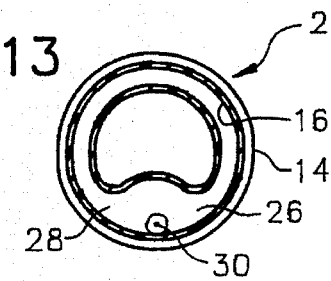
FIG. 13 is a cross-sectional view of the fourth embodiment of the present invention taken at the same location on FIG. 8 as FIG. 10 showing a fifth circumferential orientation of the chamber.

Now referring to FIGS. 10-13, exemplary cross sections of thickened portion 26, with or without internal chamber 28, are shown. Thus FIGS. 10-13 pertain to both the fourth embodiment of the present invention in which a solid is employed in thickened portion 26 and in which either a gas or a liquid is filled in internal chamber 28 of thickened portion 26. As shown in FIGS. 10 and 13, thickened portion 26 can be present around the entire circumference of facilitator 2. Alternatively, as shown in FIGS. 11 and 12, thickened portion 26 may only be present around a portion of the circumference of facilitator 2. As shown in FIG. 10, thickened portion 26 can have a substantially smooth surface. Alternatively, as shown in FIGS. 11-13, thickened portion 26 can have an inner surface which is contoured to impart most efficiently the requisite external pressure at the site on the penis of the venous leak. More specifically, as shown in FIG. 12, thickened portion 26 can be contoured such that maximum external pressure is applied to varying regions of the penis, one example being the undersurface or corpus spongiosum. Additionally, the contour of thickened portion 26 may be such that the relative height of thickened portion 26 decreases, or increases, along the longitudinal axis of the penis. It is also to be understood that thickened portion 26 can be present at only base 8 and/or central portion 12 of condom 2 (as shown in FIG. 8), or instead may extend along the entire length of facilitator 2 (as shown in FIG. 9).

Figure 14:
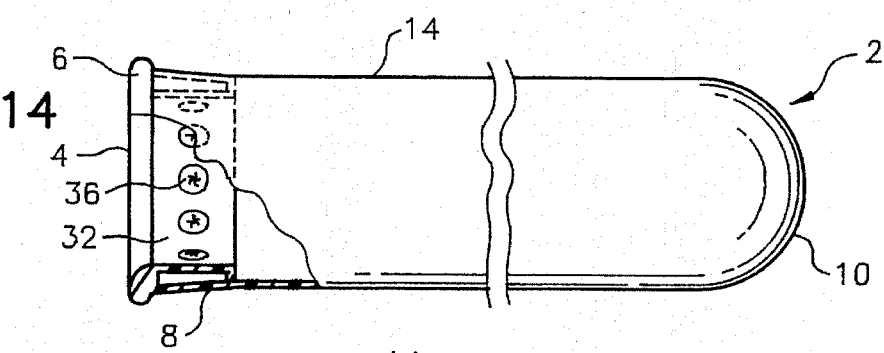
FIG. 14 is a plan view of a fifth embodiment of the present invention showing a liquid retaining chamber located at the base of the condom.
Figure 15:
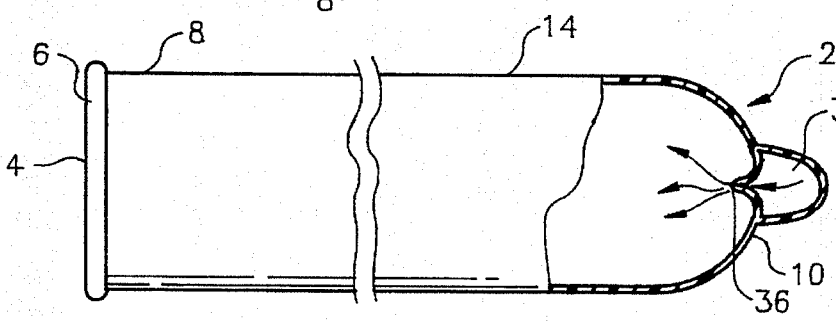
FIG. 15 is a plan view of the fifth embodiment of the present invention showing a liquid retaining chamber located at the tip of the condom.
Figure 16:
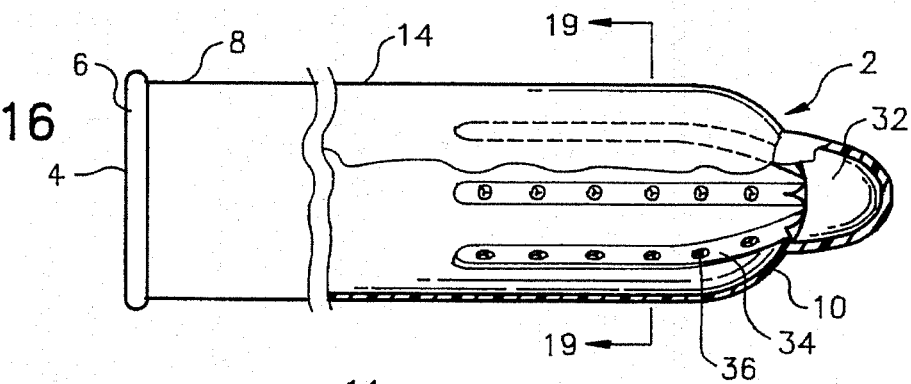
FIG. 16 is a plan view of the fifth embodiment of the present invention showing a plurality of channels communicating with the liquid retaining chamber on the tip of the condom.
Figure 18:
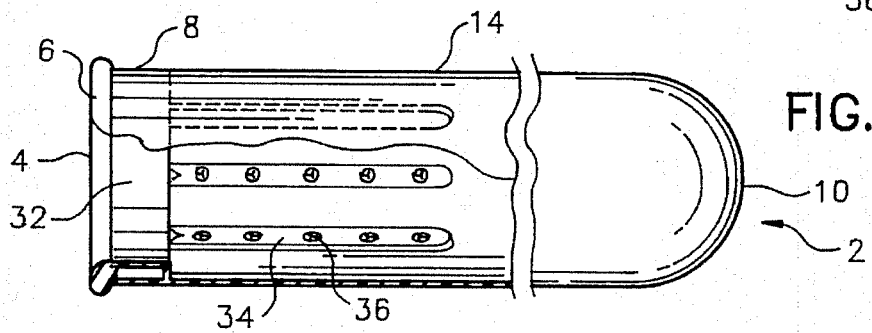
FIG. 18 is a plan view of the sixth embodiment showing a plurality of channels communicating with the liquid retaining chamber on the base portion of the condom.
Figure 17:
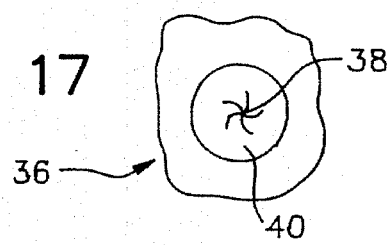
FIG. 17 is an enlarged detailed view of the one-way valve which provides communication between the liquid retaining chamber and the condom of the sixth embodiment of the present invention.

Now referring to FIGS. 14-20, a fifth embodiment of the present invention is shown in which condom 2 is adapted to dispense medication, spermicide, bactericide, anti-viral chemical compounds or the like onto the surface of the penis. Condom 2 includes a liquid retaining chamber 32 adapted to hold the above types of medications or the like. Liquid retaining chamber 32 may be oriented on base 8 of condom 2 as shown in FIG. 14, or on tip 10 of condom 2 as shown in FIG. 15. Optionally, as shown in FIGS. 16 and 18, a plurality of channels 34 longitudinally disposed on condom 2 and in communication with liquid retaining chamber 32 may be present in order to increase the area of dispersal of medication or the like onto the surface of the penis. Liquid retaining chamber 32 is partitioned from condom 2 except for communication therebetween by one-way valve 36, as shown in FIG. 17. One-way valve 36 is comprised of an orifice 38 surrounded by an area of elastomeric material 40, such as latex or the like, which constricts orifice 38 to prevent passage of medication or the like from liquid retaining chamber 32 into condom 2. Upon application of external pressure on liquid retaining chamber 32, the liquid pressure within liquid retaining chamber 32 increases such that orifice 38 is urged open and the medication or the like flows into condom 2 and onto the penis. When channels 34 are present, a plurality of one-way valves 36 may be located therein such that medication or the like in liquid retaining chamber 32 passes from liquid retaining chamber 32 into channels 34, through one-way valves 36, and into condom 2. In this configuration, the medication or the like may already be contained in channels 34, and optionally in liquid retaining chamber 32 as well, such that application of external pressure onto channels 34 releases the medication or the like.

Figure 19:
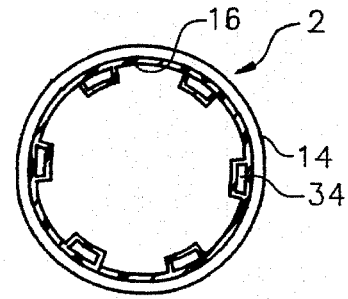
FIG. 19 is a cross-sectional view of the fifth embodiment taken along lines 19—19 of FIG. 16.
Figure 20:
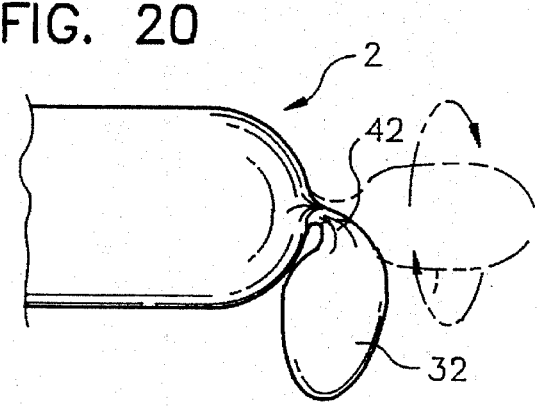
FIG. 20 is a plan view of the fifth embodiment of the present invention in which the liquid retaining chamber on the tip of the condom is foldable.

As shown in FIGS. 19 and 20, instead of one-way valve 36, medication or the like may be partitioned from condom 2 in liquid retaining chamber 32 by providing liquid retaining chamber 32 with an elongate neck 42 which is adapted to be folded upon rolling of the condom for storage prior to use. In this manner, medication or the like is partitioned from condom 2 in liquid retaining chamber 32. When the condom is unrolled for use, elongate neck 42 is likewise unfolded and the medication or the like in liquid retaining chamber 32 then passes from liquid retaining chamber 32 into condom 2 and onto the penis. Optionally, elongate neck 42 can be closed by a clamp or bendable tie 44 to partition condom 2 and liquid retaining chamber 32, instead of folding elongate neck 42.

Figure 21:
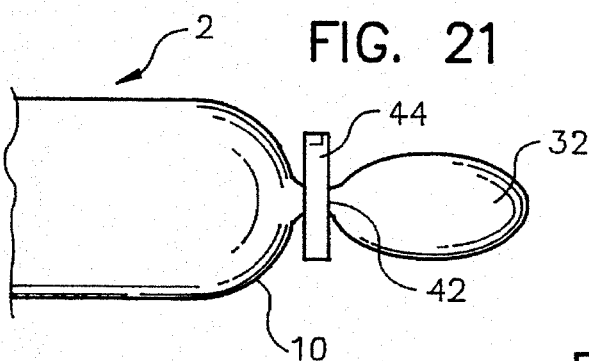
FIG. 21 is a plan view showing the liquid retaining chamber on the tip of the condom has a fastener thereon.
Figure 22:
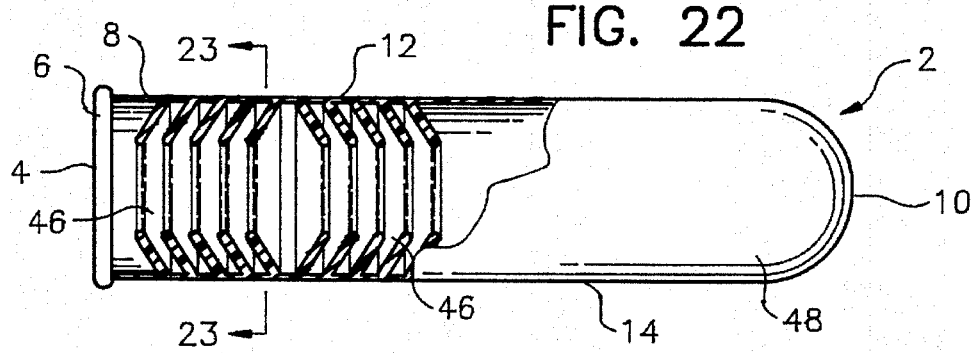
FIG. 22 is a cross-sectional view of the sixth embodiment of the present invention taken along lines 22—22 of FIG. 6 showing a plurality of annular partitions circumferentially disposed on the interior of the condom.
Figure 23:
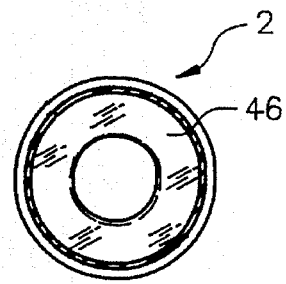
FIG. 23 is a cross-sectional view of the sixth embodiment of the present invention taken along lines 23—23 of FIG. 6.

Now describing a sixth embodiment of the present invention, as shown in FIGS. 21 and 22, condom 2 includes a plurality of annular ribs 46 circumferentially disposed on the internal surface 16 of condom 2. Preferably, a plurality of annular ribs 46 are located adjacent base 8 of condom 2 and adjacent central portion 12 of condom 2. The annular ribs 46 located adjacent base 8 are preferably disposed at an angle toward open end 4 and base 8 of condom 2 while the annular ribs 46 located adjacent central portion 12 are preferably disposed at an angle toward tip 10 of condom 2. Annular ribs 46 are preferably comprised of the same material as condom 2, such as latex or the like, and are integrally formed with condom 2. The above described preferred angled orientation of annular ribs 46 located adjacent base 8 toward open end 4 and base 8 prevents vaginal fluid from entering condom 2 during intercourse. The above described preferred orientation of annular ribs 46 located adjacent central portion 2 toward tip 10 likewise prevents semen in condom 2 from exiting therefrom during intercourse. Thus, annular ribs 46 prevent the exchange of bodily fluids during sexual intercourse. Annular ribs 46 are preferably of variable length and thickness in order to maximize the above described partitioning of bodily fluids.

FIG. 22 also shows a seventh embodiment of the present invention, which can be employed alone, with the sixth embodiment, or with any of one or more of the other embodiments. In this seventh embodiment, condom 2 is sheathed with an external layer of hydrophobic or hydrophilic material 48 over external surface 14 by a layering process known in the art. All, or only a portion of condom 2 can be covered by hydrophobic or hydrophilic material 48 such that, for example, either circumferential or longitudinal strips of hydrophobic or hydrophilic material 48 may be present. Hydrophobic or hydrophilic material 48 may be any material capable of reducing the frictional coefficient of condom 2 during intercourse when hydrophobic or hydrophilic material 48 contacts water, vaginal fluids or other hydrophilic liquids. When hydrophobic, material 48 is preferably comprised of either a flouropolymer (most preferably tetraflouroethylene) or a propylene compound (most preferably flouroethylpropylene). When hydrophilic, material 48 is preferably comprised of an acrylic copolymer (most preferably hydroxymethylmethacrylate (HEMA) or polyacrylamide), a hydrogel, a vinylpolymer (most preferably polyvinylpyrrolidone) or an aliphatic polyether (most preferably polyethylene oxide).

While preferred embodiments of the invention have been illustrated and described, it will be appreciated that various changes can be made therein without departing from the spirit and scope of the invention.

I claim:

1. A device for assisting in establishing and maintaining male erectile function comprising:

an elastic open ended sheath adapted to fit onto a flaccid or partially flaccid penis; and a plurality of woven strands in said sheath, the length and arangement of said woven strands being based on the diameter of the penis to realize in the penis when erectile a selective constriction around and/or along selected portions of the penis to not impede arterial blood flow to the penis but impede venous blood flow from the penis and thereby maintain the penis in an erectile condition, said woven strands being in the form of an open weave so that said strands can move individually relative to one another.

2. The device of claim 1 wherein said woven strands are interwoven both longitudinally on and axially around said elastic sheath.

3. The device of claim 1 wherein said woven strands are interwoven only longitudinally on said elastic sheath.

4. The device of claim 1 wherein said woven strands are interwoven only axially around said elastic sheath.

5. The device of claim 1 wherein said woven strands are hollow.

6. The device of claim 1 wherein said woven strands are solid.

7. The device of claim 1 wherein at least a first portion of said woven strands have a diameter varied from the diameter of a second portion of said woven strands.

8. The device of claim 1 wherein said woven strands form a weave, said weave having a circumference around said sheath which varies along the length of said sheath.

9. A device for assisting in establishing and maintaining male erectile function comprising:

an open ended elastic sheath adapted to fit onto a flaccid or partially flaccid penis, said elastic sheath comprising a plurality of woven strands in an open weave configuration, the length and arrangement of said strands being such as to permit the strands to move longitudinally individually one another, the sheath causing in the penis when erectile a selective constriction around and/or along selected portions of the penis by differential external pressures applied to said selected portions of the penis so as to not impede arterial blood flow to the penis but impede venous blood flow from the penis and thereby establish and maintain the penis in an erectile condition.

10. The method of assisting in the establishment and maintenance of male penis erectile function, comprising:

selecting for installation on a flaccid or partially flaccid penis an erectile facilitator in the form of an elastic sheath of a nominal length and diameter to realize in the penis when erect a selective differential pressure constriction around and/or along selected portions of the penis, said facilitator being characterized by having portions thereof made up of woven strands interwoven yet individually relatively movable in directions extending in both longitudinal and circumferential directions in the sheath so as to be subject to elongation and/or expansion thereof responsive to increases in size of portions of the penis;

installing said sheath on the flaccid or partially flaccid penis; and maintaining said sheath in position on the penis while maintaining arterial blood flow to the penis, with selective constrictions of selective portions of the penis by the sheath acting to not impede arterial blood flow to the penis but impede venous blood flow from the penis and thereby enable the establishment and maintenance of the penis in an erectile condition.

11. The method of claim 10, comprising applying selective differential pressure to a portion of the penis not relatively as erectile as other portions thereof by engaging such less erectile penis portion with a portion of the sheath which is less elastic than other portions with the result that greater external pressure is applied to said relatively less erectile penis portion than is applied to said other portions of the penis.

* * * * *